United States Patent [19]

Hogen Esch

[11] Patent Number: 5,372,133
[45] Date of Patent: Dec. 13, 1994

[54] IMPLANTABLE BIOMEDICAL SENSOR DEVICE, SUITABLE IN PARTICULAR FOR MEASURING THE CONCENTRATION OF GLUCOSE

[75] Inventor: Johannes H. L. Hogen Esch, Aalten, Netherlands

[73] Assignee: N.V. Nederlandsche Apparatenfabriek Nedap, De Groenlo, Netherlands

[21] Appl. No.: 12,860

[22] Filed: Feb. 3, 1993

[30] Foreign Application Priority Data

Feb. 5, 1992 [NL] Netherlands ................ 9200207

[51] Int. Cl.$^5$ ............... A61B 5/07; A61B 5/00
[52] U.S. Cl. ................ 128/631; 128/642; 128/903
[58] Field of Search ........... 128/632, 633, 634, 637, 128/642, 899, 903, 631; 604/890.1, 891.1

[56] References Cited

U.S. PATENT DOCUMENTS

| | | | |
|---|---|---|---|
| 3,837,339 | 9/1974 | Aisenberg et al. | 128/903 X |
| 4,196,418 | 4/1980 | Kip et al. | 340/152 T |
| 4,655,880 | 4/1987 | Liu | 204/1 T |
| 4,703,756 | 11/1987 | Gough et al. | 128/635 |
| 4,781,798 | 11/1988 | Gough | 128/635 X |
| 4,805,624 | 2/1989 | Yao et al. | 128/635 |
| 4,944,299 | 7/1990 | Silvian | 128/903 X |
| 5,070,535 | 12/1991 | Hochmair et al. | 128/903 X |

FOREIGN PATENT DOCUMENTS

| | | |
|---|---|---|
| 0245073 | 11/1987 | European Pat. Off. . |
| 0453283 | 10/1991 | European Pat. Off. . |
| 9101680 | 2/1991 | WIPO ................ 128/632 |
| WO91/04704 | 4/1991 | WIPO . |

OTHER PUBLICATIONS

Hepato-Gastroenterology, vol. 31, No. 6, Dec. 1984, pp. 285–288.

Primary Examiner—Lee S. Cohen
Assistant Examiner—Samuel Gilbert
Attorney, Agent, or Firm—Jacobson, Price, Holman & Stern

[57] ABSTRACT

Implantable biomedical sensor device for measuring in vivo the presence and/or concentration of physiological substances, such as the concentration of glucose, in a human or animal body. A miniaturized electronic responder (1) arranged in a closed housing (2) of biocompatible material in an electromagnetic interrogation field is capable of contactlessly exchanging binary coded information with a transmitter/receiver, and includes electrical connections (4, 5, 6) passed through the wall of the housing, at least a work electrode (10), a counter-electrode (8) and preferably also a reference electrode (9) outside the housing. The work electrode includes a membrane (13) with hollow fibers extending transversely to the surface of the membrane and having internal walls coated with a conductive polymer (15) and in which a redox enzyme (16) is disposed. One end of the hollow fibers is in electrical contact with a processing device (20) which converts the signals supplied by the work electrode in operation to binary signals.

28 Claims, 2 Drawing Sheets

IMPLANTABLE BIOMEDICAL SENSOR DEVICE, SUITABLE IN PARTICULAR FOR MEASURING THE CONCENTRATION OF GLUCOSE

BACKGROUND OF THE INVENTION

This invention relates to an implantable biomedical sensor device for measuring in vivo the presence and/or concentration of physiological substances, in particular the concentration of glucose, in a human or animal body.

The traditional glucose sensors are based on the oxidation of glucose by oxygen in the presence of the redox enzyme glucose oxidase (GOd). The flavin adenine dinucleotide (FAD) center of glucose oxidase is reduced to FADH by glucose (reaction 1). The regeneration of the enzyme occurs through reduction of oxygen to hydrogen peroxide (reaction 2).

$$GOd\text{-}FAD + glucose \rightarrow GOd\text{-}FADH2 + gluconate \quad (1)$$

$$GOd\text{-}FADH2 + O2 \rightarrow GOd\text{-}FAD + H2O2 \quad (2)$$

The enzyme glucose oxidase is immobilized in gels or membranes which cover an electrode. The glucose content is determined indirectly in one of the following ways:

1. Detection of the decrease in oxygen with a Clark oxygen electrode.

A great disadvantage of this method is the sensitivity to the oxygen pressure of the environment.

2. Detection of the hydrogen peroxide production with a hydrogen peroxide electrode.

A drawback of this technique is that hydrogen peroxide degrades the redox enzyme. Another drawback is the high voltage that must be applied, rendering the sensor sensitive to other electroactive components (for instance ascorbic acid) present in biological fluids. Often, biological fluids also contain the enzyme catalase, which breaks down hydrogen peroxide.

In a second generation of glucose sensors, mediators (ferrocene and derivatives) are utilized, which provide for the electron transfer between the redox enzyme and the electrode. The advantage of the use of mediators is that the measurement can be performed at a relatively low voltage, e.g. 350 mV, instead of 800 mV. As a result, by-reactions contribute to a lesser extent to the total current measured. The regeneration of the reduced flavin in glucose oxidase occurs through reduction of the mediator (reaction 3). The reduced mediator is subsequently oxidized electrochemically (reaction 4).

$$GOd\text{-}FADH2 + 2\ MedOx \rightarrow GOd\text{-}FAD + 2\ MedRed + 2\ H+ \quad (3)$$

$$2\ MedRed \rightarrow 2\ MedOx + 2\ electrons\ (at\ the\ anode) \quad (4)$$

Sensors which are based on this principle have the disadvantage that the mediator disappears from the system. Moreover, usable mediators are often toxic, rendering in vivo measurement impossible. Recently, TNO (Dutch Organization for Applied Scientific Research) and the Catholic University of Nijmegen have developed a third generation of glucose sensors, involving direct electron transfer between the redox enzyme and an electrode via a conductive polymer. The basis of the sensor is a filtration membrane having cylindrical pores (Cyclopore, pore diameter 600 nm). By a specially developed polymerization process, tile pores of the membrane are coated with polypyrrole, so that hollow fibers of conductive polymer extend perpendicularly through the membrane and are in contact with the measuring fluid. The glucose oxidase is immobilized in the fibers, permitting direct electron transfer between the redox enzyme and the polymer. The location of the enzyme in the pores further provides protection of the enzyme against any influences of the environment, so that it can retain its active structure. After the enzyme has oxidized a glucose molecule (reaction 1), the reduced enzyme can be re-oxidized by transferring electrons to the conductive polymer.

It is noted that implantable electronic responders per se are already known. Dutch patent application 8701541, for instance, discloses the use of an implantable responder for the identification of livestock. Also, implantable responders are already utilized in practice for the identification of cattle and pigs. The known implantable responders are arranged in a glass tube melted up at its ends and comprise a resonant circuit whose coil at least partly constitutes the antenna for receiving an electromagnetic interrogation field generated by a transmitter or a transmitter/receiver. The interrogation field can bring the resonant circuit into resonance and the alternating voltage generated across the resonant circuit is used, after being rectified, as supply voltage for the digital circuits of the responder. The digital circuits comprise a code signal generator and can further comprise a clock pulse shaper. However, the clock pulses can also be derived directly from the tops of the alternating voltage across the resonant circuit. After receiving supply voltage and clock pulses, the code signal generator generates a binary code signal, which is used to control a switching means, for instance a transistor. The switching means is connected to the resonant circuit and can modulate the resonant frequency and/or the damping of the resonant circuit in the rhythm of the binary code signal. This modulation can be detected by a transmitter/receiver or by a separate receiver. These techniques are known per se. One example of a suitable responder is disclosed in U.S. Pat. No. 4,196,418, which is considered to be incorporated herein as a reference.

BRIEF SUMMARY OF THE INVENTION

In vitro experiments have shown that glucose concentrations can be measured continuously and accurately for a long time without any loss of sensitivity with a sensor based on a membrane with hollow fibers in which the redox enzyme is located and whose walls are coated with a polypyrrole, this membrane being further provided, on one side thereof, with a platinum film that serves as an electrode. Such a glucose sensor is independent of the oxygen concentration and insensitive to substances such as fructose, citrate, lactate, pyruvate, urea and urea acid.

The object of the present invention is to provide an implantable, contactless, readable glucose sensor device which utilizes a sensor of the third generation as described above.

To that end, according to the invention, an implantable biomedical sensor device of the type described above is characterized by a miniaturized electronic responder, which in an electromagnetic interrogation field, is capable of contactlessly exchanging binary coded information with a transmitter/receiver, this responder being arranged in a closed housing of biocompatible material; and by at least two, but preferably three, electrical connections, passed through the wall of the housing, which constitute electrodes outside the housing, these electrodes comprising at least a work electrode and a counter-electrode, the work electrode comprising a membrane with hollow fibers which extend transversely to the surface of the membrane and whose internal walls are coated with a conductive polymer and in which a redox enzyme is located and which, at one end thereof, are in contact with the associated electrical connection, this electrical connection being coupled to a processing device which receives the signals supplied by the work electrode in operation and converts these signals into binary signals. In order to provide a constant voltage between the fluid and the work electrode, it is preferred that a third electrode is arranged, for instance an Ag/AgCl reference electrode.

It is further noted that a biomedical sensor device according to the invention can naturally be used for measurement in vitro as well.

BRIEF DESCRIPTION OF THE DRAWINGS

Hereinafter, the invention will be further described, by way of example only, with reference to the accompanying drawings of one exemplary embodiment wherein.

DETAILED DESCRIPTION

Figure 1:
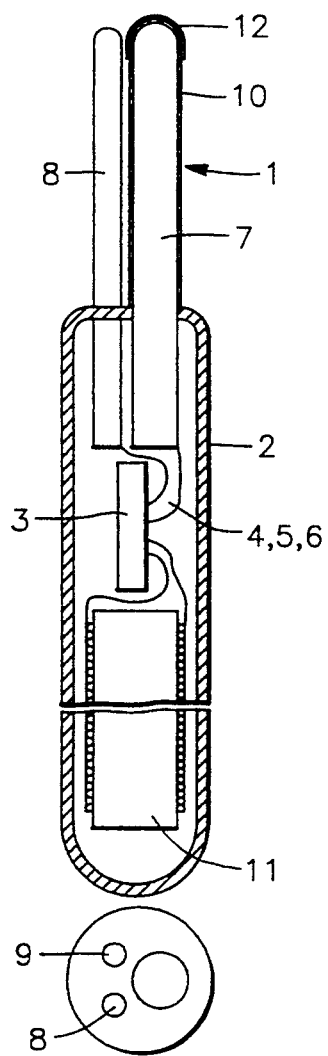
FIG. 1 is a schematic cross-sectional and top plan view which shows on an enlarged scale an example of an implantable sensor device according to the invention.

FIG. 1 schematically shows an example of an implantable sensor device 1 according to the invention. The sensor device comprises a capsule 2, which, Ln the embodiment shown, consists of a glass tube which has been melted up at both ends. However, any other biocompatible and permanently fluid-tight material is usable. It is also possible to use a different shape than a tubular shape. A tubular shape, however, permits ready implantation by means of a hollow needle.

Disposed in the capsule is the electronic circuit 3 of the responder. The electronic circuit is connected to the electrodes located outside the capsule by means of a plurality of electrical connections. In the embodiment shown, three connections 4, 5 and 6 with associated electrodes 7, 8 and 9 are used. In the embodiment shown, the electrodes 7, 8 and 9 project from the end of the capsule.

Electrode 8 is the counter-electrode, which may be made of a suitable noble metal, such as for instance platinum, or may be coated with such a metal. Electrode 9 is an Ag/AgCl reference electrode providing for a constant voltage between the work electrode and the fluid.

The work electrode 10 is a composite electrode, comprising a membrane with cylindrical pores. A suitable membrane is for instance the membrane available under the name of Cyclopore. The pore diameter may for instance be 600 nm. The pores constitute hollow fibers extending transversely to the surfaces of the membrane.

To protect the tip of the work electrode, a cap 12 may be arranged, which is made of a biocompatible plastics material suitable for the purpose.

Figure 2:
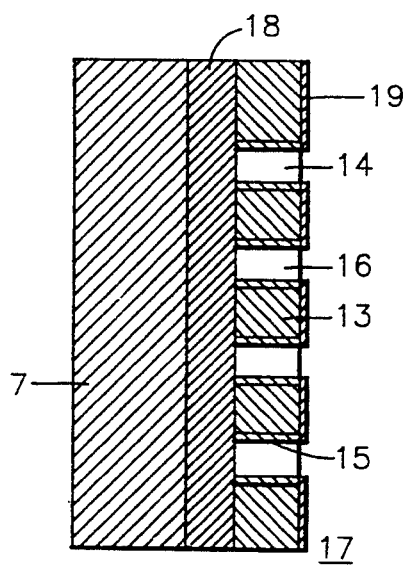
FIG. 2 is a schematic cross-sectional view which shows on a yet further enlarged scale a part of the sensor device of FIG. 1.

The surface of the work electrode is shown in more detail in FIG. 2. The walls of the hollow fibers 14 are coated with an electrically conductive polymer layer 15, for instance made of polypyrrole. In the pores, the redox enzyme glucose oxidase is immobilized, as indicated at 16, so that direct electron transfer between the redox enzyme and the polymer layer is possible. In the pores, the enzyme is protected against ambient influences, yet communicates with the body fluids 17 present around the sensor device.

It is noted that it is already known from the literature that there is a clear relationship between the glucose concentration ill the blood stream and the glucose concentration in the tissue. Accordingly, measurement of the glucose concentration with the aid of a sensor device implanted in the tissue is equivalent to direct measurement in the blood stream. On one side of the membrane, the hollow fibers of the membrane 13 are connected to the core 7 of the work electrode. For that purpose, a conductive layer 18 is provided on that side of the membrane. The conductive layer 18 may for instance consist of a thin layer of platinum of a suitable thickness. The thickness of the platinum layer is not critical and may for instance be between 50 and 400 nm. The platinum film is in direct or indirect electrical contact with the core 7 of the work electrode, which has been passed through the wall of the capsule 2 so as to be sealed relative thereto. The platinum layer can for instance be applied to the membrane by sputtering.

In order to improve the biocompatibility of the sensor device, the side of the membrane that comes into contact with the body fluids can be provided with a film 19 of a suitable metal or a suitable plastics, such as for instance high-density poly-lactic acids. If a metal film is applied, this may for instance be a platinum film, applied through sputtering. It has been found that if the sputtered layer has a thickness of 100 nm, the men, rate is still sufficiently porous to allow the desired interaction between the glucose and the redox enzyme. It is also possible to use, for instance, titanium, instead of platinum. An advantage of a metal covering layer is that it can be connected to the counter-electrode 8 at the same time so as to realize the desired potential difference across the membrane.

A potential difference of 0.35 volts provides good results. If the contact surface between the membrane and the fluid has an area of no more than 15 $mm^2$ and the potential difference is 0.35 volts, currents of the order of 100–1,000 nA are measured. This means that the contact surface and/or the potential difference can be reduced still further. It has been found that the operation of a sensor device as described above is independent of the oxygen concentration as well as the presence of fructose, citrate, lactate, pyruvate, glutathione, urea and urea acid in mM concentrations. Ascorbic acid, however, is capable of influencing the measuring result. This problem can be solved by measuring at a lower potential difference of, for instance, about 0.20 volts and/or by the use of a permselective second membrane, covering the electrode 10 with the membrane 19. For purposes of this description, the term "permselective" means a membrane having selective permeability which is well known as the property of a membrane or other material that allows some substances to pass through it more easily than others. This second membrane is impermeable to the charged ascorbic acid, but permeable to the neutral glucose molecule and the oxidation product of glucose (gluconolactone).

Figure 4:
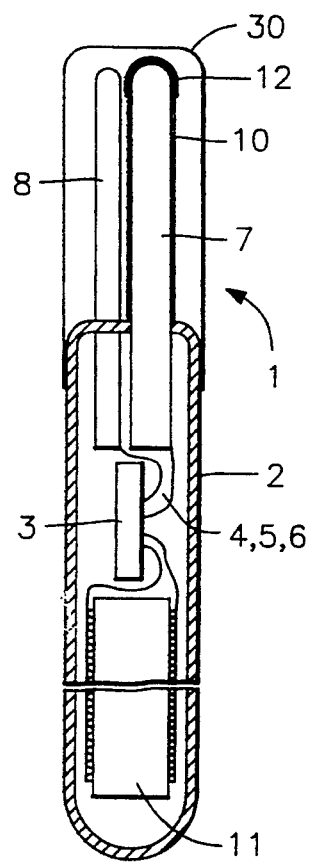
FIG. 4 is a view similar to FIG. 1 which shows a modification of the device of FIG. 1.

If so desired, the permselective membrane can be alternatively constructed as a cap surrounding all electrodes, which is arranged on the capsule. Such a cap is shown at 30 in FIG. 4. The cap 30 surrounds the electrodes 7, 8 and 9 with some clearance. The body fluid, at any rate certain components thereof, such as glucose, can penetrate into this space between the cap and the electrodes.

Alternatively, it is possible to measure with the aid of two electrodes of which only one contains the redox enzyme. The influence of other electroactive molecules can then be eliminated and the differential signal can then be unequivocally ascribed to the glucose.

Figure 3:
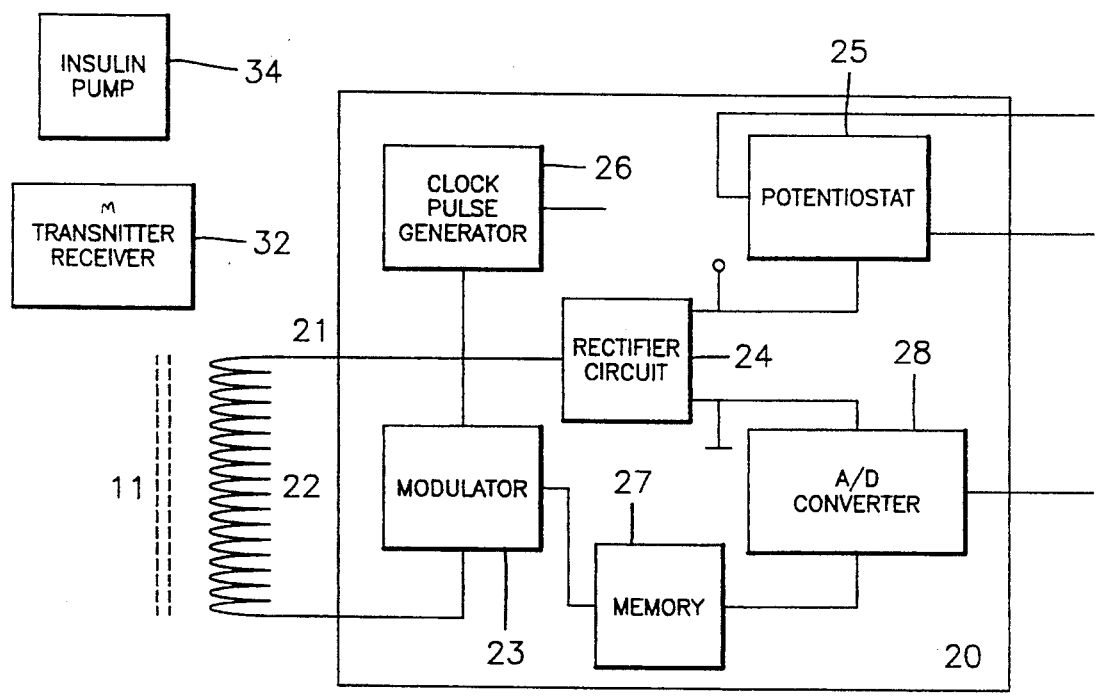
FIG. 3 is an example of an electrical block diagram of a sensor device according to the invention.

FIG. 3 schematically shows a responder circuit 20 for a sensor device according to the invention. The responder circuit comprises an input circuit 21 with a coil 22 which or may not be tuned with the aid of a capacitor. The coil 22 may be provided with a ferrite core 11 and at the same time constitutes an antenna. The input circuit 21 is corrected with a rectifier circuit 24 producing a preferably stabilized supply voltage starting from the voltage induced by an interrogation field in the input circuit in operation. The supply voltage is applied to the various active components of the responder circuit 20. Further, starting from the supply voltage, the measuring voltage to be set across the membrane in operation is formed, for instance by means of a so-called potentiostat 25.

The responder circuit can further comprise a clock pulse generator 26, capable of providing clock pulses for the control of the digital circuits. In principle, it is also possible to use the tops of the alternating voltage induced in the receiver circuit as clock signals. If the responder circuit is provided with an identification code, this code is stored in a memory 27. The memory may be wirelessly programmable. In that case, a demodulator, which is not shown in FIG. 3, is connected between the receiver circuit and the memory. FIG. 3 does show all A/D converter 28, which receives the current signals supplied by the work electrode 10 and converts them to the binary signals which can be stored in the memory 27 or a part thereof. In operation, the output signals of the memory are applied to a modulation means 23, which may for instance be a switching means, capable of modulating the electrical properties of the receiver circuit and hence the energy absorption of the receiver circuit.

Instead of the memory and the A/D converter, a microprocessor could be used. The measured signals are preferably represented as binary signals of eight bits or more.

The electrode 10 can in principle be arranged on a curved surface at the ends of the capsule or on a flattened part, but is preferably arranged on a projecting electrode part 7.

Further, the responder circuit described is a passive circuit, which means that the required supply energy is drawn from the interrogation field. It is also possible, however, to arrange a battery in the capsule.

The sensor device can be activated by bringing a transmitter/receiver such as shown schematically at 32, preferably of portable design, into the vicinity of the implanted sensor device to generate an electromagnetic interrogation field having a frequency that is suitable for the sensor device in question. After being activated, the sensor device can measure the glucose concentration in the surrounding tissue by means of the current generated by the membrane electrode 10. The current intensity is converted by the A/D converter to a digital signal, which, alone or together with a binary code, is used to modulate the energy absorption of the receiver circuit. This modulation is detected by the transmitter/receiver and converted to a measured value.

If the sensor device comprises a so-called battery, the measuring signal could alternatively be optionally emitted via a separate antenna coil. This, however, requires a sensor device of greater dimensions, which may be objectionable.

The value of the glucose content as detected by the transmitter/receiver can be used to control an insulin pump, if necessary such as shown schematically at 34. If an implanted insulin pump is used, this pump, too, can in principle be wirelessly energized with the same transmitter/receiver or a special transmitter.

For measurement, preferably the chrono-amperometry technique is used. According to this technique, the instantaneous current intensity is measured at a predetermined time after the occurrence of a potential jump. This predetermined time may be prior to the time at which a stable final condition has been reached, that is, if the relation is known between the measured value at the time chosen and the measured value in the stable final condition.

In the case where the glucose concentration in the tissue is measured, after the voltage has been switched on, the current in the work electrode is measured at a time halfway between the time of activation and the time at which the stable condition is reached. This is the so-called half-value time $t_{\frac{1}{2}}$. The half-value time may be fixed in the responder itself by means of a suitable timer circuit, for instance a shift register or a counter, or may be determined in the transmitter/receiver or by the user. This technique enables a faster measuring procedure and, moreover, the redox enzyme is brought in the activated condition only for a short time. It is expected that this technique will contribute to a long life of the sensor device.

It is noted that, after the foregoing, various modifications will readily occur to a person of ordinary skill in the art. Thus, various embodiments of the responder circuit are possible. It is also possible to measure the presence and/or concentration of other substances, for instance lactose, in the human or animal body or in vitro, in the manner described, with the aid of a suitable enzyme. Such modifications are understood to fall within the scope of the present invention.

I claim:

1. An implantable biomedical sensor device for measuring in vivo a presence and/or concentration of physiological substances in an animate body comprising:
    a miniaturized electronic responder responsive to an electromagnetic interrogation field for contactlessly exchanging binary coded information with a transmitter/receiver;
    a closed housing of bio-compatible material having qt least one wall, said responder being disposed in said closed housing;
    a work electrode having at least a part thereof disposed outside of said housing and comprising a membrane having at least one surface, hollow fibers in said membrane extending transversely to said at least one surface of said membrane and having internal walls and ends thereon, a coating of conductive polymer on said internal walls, and a redox enzyme disposed in said hollow fibers;

a processing device in said housing for receiving signals from said work electrode in operation and converting said signals to binary signals;

electrical connection means between one of said ends of said hollow fibers and said processing device for conducting said signals from said work electrode to said processing device;

a counter-electrode at least a part thereof disposed outside of said housing; and electrical connection means for connecting said counter-electrode and said processing device.

2. The implantable sensor device as claimed in claim 1 and further comprising:
a reference electrode mounted on said housing and having at least a part thereof disposed outside of said housing.

3. The implantable sensor device as claimed in claim 2 wherein:
said reference electrode is an Ag/AgCl electrode.

4. The implantable sensor device as claimed in claim 2 and further comprising:
a permselective bio-compatible membrane on said reference electrode.

5. The sensor device as claimed in claim 2 wherein:
said responder comprises a potentiostat for generating in operation a stable voltage between said reference electrode and said work electrode.

6. The implantable sensor device as claimed in claim 1 and further comprising:
a thin conductive layer on one side of said membrane and electrically connected with said electrical connection means connecting said work electrode to said processing device.

7. The implantable sensor device as claimed in claim 6 wherein:
said thin conductive layer is a metal layer.

8. The implantable sensor device as claimed in claim 7 wherein said metal layer is a platinum layer.

9. The implantable sensor device as claimed in claim 6 wherein:
said thin conductive layer is a sputter applied metal layer.

10. The implantable sensor device as claimed in claim 29 wherein:
said work electrode further comprises a projecting electrode core, said membrane being mounted on said electrode core.

11. The implantable sensor device as claimed in claim 1 and further comprising:
an outer wall on said housing;
a thin conductive layer on said outer wall of said housing; and
said membrane being on said thin conductive layer so that said thin conductive layer is interposed between said outer wall of said housing and said membrane.

12. The implantable sensor device as claimed in claim 1 and further comprising:
a free surface on said membrane; and
a coating of a thin layer of bio-compatible material on said free surface of said membrane.

13. The implantable sensor device as claimed in claim 12 wherein:
said bio-compatible material is a synthetic material.

14. The implantable sensor device as claimed in claim 12 wherein:
said bio-compatible material is a sputtered applied metal layer.

15. The implantable sensor device as claimed in claim 14 and further comprising:
means for connecting said bio-compatible metal layer counter-electrode.

16. The sensor device as claimed in claim 1 and further comprising:
a flattened part on said housing, said membrane of said work electrode being disposed on said flattened part.

17. The implantable sensor device as claimed in claim 1 and further comprising:
a permselective second membrane covering said membrane having said hollow fibers therein.

18. The implantable sensor device as claimed in claim 17 wherein:
said second membrane comprises a cap enclosing said electrodes and connected to said housing.

19. The implantable sensor device as claimed in claim 1 and further comprising:
a second work electrode comprising a membrane, hollow fibers in said membrane having internal walls, and a coating of a conductive polymer on said internal walls; and
said processing device comprises means for shaping a difference of signals supplied by said work electrodes.

20. The implantable sensor device as claimed in claim 1 wherein:
said conductive polymer is polypyrrole.

21. The implantable sensor device as claimed in claim 1 and further comprising:
means in said responder for generating in operation a stable maximum voltage of substantially 0.35 volts across said membrane.

22. The implantable sensor device as claimed in claim 1 wherein:
said responder comprises a timer circuit for measuring a signal supplied by said work electrode at a predetermined time after activation of said responder.

23. The sensor device as claimed in claim 1 and further comprising:
means in said responder for generating a predetermined voltage in response to said electromagnetic interrogation field so that said responder is a passive responder.

24. The sensor device as claimed in claim 1 and further comprising:
battery means in said responder for providing a predetermined voltage for operation thereof.

25. A system comprising:
at least one implantable biomedical sensor device as claimed in claim 29; and
at least one transmitter/receiver means for generating an electromagnetic interrogation field for activating said at least one sensor device and reading out said sensor device.

26. The system as claimed in claim 25 and further comprising:
an electrically controllable insulin pump operatively connecteable to said transmitter/receiver means so that operation of said pump is controlled by said transmitter/receiver means in response to signals produced by said responder.

27. A biomedical sensor device for assaying in vitro a presence and/or concentration of physiological substances comprising:
- a miniaturized electronic responder responsive to an electromagnetic interrogation field for contactlessly exchanging binary coded information with a transmitter/receiver;
- a closed housing of bio-compatible material having at least one wall, said responder being disposed in said closed housing;
- a work electrode passing through said at least one wall of said housing and comprising an outer part outside of said housing, a membrane having at least one surface, hollow fibers in said membrane extending transversely to said at least one surface of said membrane and having internal walls and ends thereon, a coating of conductive polymer on said internal walls, and a redox enzyme disposed in said hollow fibers;
- a processing device in said housing for receiving signals from maid work electrode in operation and converting said signals to binary signals;
- electrical connection means between one of said ends of said hollow fibers and said processing device for conducting said signals from said work electrode to said processing device;
- a counter-electrode extending through said at least one wall of said housing and having an outer part outside of said housing; and
- electrical connection means for connecting said counter-electrode end said processing device.

28. The sensor device as claimed in claim 27 and further comprising:
- means in said responder for generating a predetermined voltage in response to said electromagnetic interrogation field so that said responder is a passive responder.

* * * * *